United States Patent
Lagowski et al.

(10) Patent No.: US 6,815,974 B1
(45) Date of Patent: Nov. 9, 2004

(54) DETERMINING COMPOSITION OF MIXED DIELECTRICS

(75) Inventors: Jacek Lagowski, Tampa, FL (US); Marshall D. Wilson, Tampa, FL (US); John D'Amico, Temple Terrace, FL (US); Alexandre Savtchouk, Tampa, FL (US); Lubomir L. Jastrzebski, Clearwater, FL (US)

(73) Assignee: Semiconductor Diagnostics, Inc., Tampa, FL (US)

( * ) Notice: Subject to any disclaimer, the term of this patent is extended or adjusted under 35 U.S.C. 154(b) by 0 days.

(21) Appl. No.: 10/619,170

(22) Filed: Jul. 14, 2003

(51) Int. Cl.[7] .............................................. G01R 31/26
(52) U.S. Cl. ...................................... 324/766; 324/717
(58) Field of Search ............................... 324/765, 760, 324/158.1, 750, 455, 766, 717, 716; 438/18, 14, 17

(56) References Cited

U.S. PATENT DOCUMENTS

| | | | |
|---|---|---|---|
| 4,015,203 A | 3/1977 | Verkuil | 324/158 D |
| 4,326,165 A | 4/1982 | Szedon | 324/148 R |
| 4,780,680 A | 10/1988 | Reuter et al. | 324/455 |
| 4,812,756 A | 3/1989 | Curtis et al. | 324/158 R |
| 4,978,915 A | 12/1990 | Andrews, Jr. et al. | 324/158 R |
| 5,216,362 A | 6/1993 | Verkuil | 324/158 D |
| 5,485,091 A | 1/1996 | Verkuil | 324/455 |
| 5,498,974 A | 3/1996 | Verkuil et al. | 324/767 |
| 5,519,334 A | 5/1996 | Dawson | 324/765 |
| 5,594,247 A | 1/1997 | Verkuil et al. | 250/326 |
| 5,644,223 A | 7/1997 | Verkuil | 324/158.1 |
| 5,773,989 A | 6/1998 | Edelman et al. | 324/765 |
| 6,011,404 A | 1/2000 | Ma et al. | 324/765 |
| 6,037,797 A | 3/2000 | Lagowski et al. | 324/766 |
| 6,044,102 A | 3/2000 | Labeyrie | 372/96 |
| 6,114,865 A | 9/2000 | Lagowski et al. | 324/755 |
| 6,202,029 B1 | 3/2001 | Verkuil et al. | 702/64 |
| 6,448,804 B2 | 9/2002 | Miller et al. | 324/765 |
| 6,451,686 B1 * | 9/2002 | Ngai et al. | 438/623 |
| 6,538,462 B1 * | 3/2003 | Lagowski et al. | 324/765 |

* cited by examiner

Primary Examiner—David Zarneke
Assistant Examiner—Trung Q. Nguyen
(74) Attorney, Agent, or Firm—Fish & Richardson P.C.

(57) ABSTRACT

Techniques for determining the composition of mixed dielectric layers are disclosed.

24 Claims, 7 Drawing Sheets

DETERMINING COMPOSITION OF MIXED DIELECTRICS

TECHNICAL FIELD

This invention relates to semiconductor wafer testing, and more particularly to determining the composition of a dielectric layer.

BACKGROUND

Thin dielectric layers (e.g., less than about 10 nm thick, such as about 2.0 nm thick or less) are widely used in semiconductor devices that are the building blocks of integrated circuits. For example, a thin dielectric typically separates a gate electrode from a channel region in a field effect transistor (FET).

The ever-shrinking dimensions of semiconductor devices demand increasingly thin dielectric layers. Presently, advanced devices use dielectric layers with a 1.3 nm effective thickness, however, industry analysts expect that devices will use 1.0 nm thick dielectric layers in 2006, and 0.5 nm in 2014 (see International Technology Roadmap for Semiconductors 2002 Update, available at the website public.itrs.net).

Dielectric layers are commonly formed from silicon dioxide ($SiO_2$), which can exhibit large leakage current when the layers are very thin. Such leakage is undesirable in most semiconductor devices. In FET's, for example, thin dielectric layers with large leakage currents could cause computer microprocessors to overheat and/or batteries in portable electronic equipment (e.g., notebook computers, PDA's, and mobile phones) to drain rapidly.

One solution to leakage problems associated with thin dielectric layers is to replace $SiO_2$ with other dielectric materials, called high-k dielectrics, which have a higher dielectric constant than $SiO_2$. Candidate high-k dielectrics that show promise in applications demanding thin dielectric layers include mixed dielectrics, such as "oxynitrides," which include silicon, oxygen, and nitrogen. In order to reliably manufacture high-k mixed dielectric layers at high production yields, manufacturers will most likely desire metrology methods compatible with their manufacturing techniques that can accurately and rapidly characterize the layers.

SUMMARY

In general, in a first aspect, the invention features a method for determining a composition of a dielectric layer on a semiconductor substrate, which includes monitoring a voltage across the dielectric layer under conditions where substantial leakage current flows across the dielectric layer, determining a leakage voltage for the dielectric layer from the monitored voltage, and determining the composition of the dielectric layer by comparing the leakage voltage to a reference voltage corresponding to the leakage voltage of a dielectric layer of known composition.

Implementations of the method may include one or more of the following features and/or features of other aspects.

The conditions where substantial leakage current flows across the dielectric layer can be achieved by depositing an electric charge on a surface of the dielectric layer using a corona discharge. The voltage across the dielectric layer can be monitored using a vibrating probe placed in proximity to the surface of the dielectric layer.

The dielectric layer can include first and second component materials, and the voltage across the dielectric layer can be monitored for a polarity at which current-voltage characteristics for the first and second component materials differ the most.

In general, in another aspect, the invention features a method for determining a composition of a test dielectric layer on a semiconductor substrate, which includes measuring a leakage voltage, $V_T$, at a first polarity for the test dielectric layer, comparing $V_T$ to a reference leakage voltage, $V_R$, corresponding to a leakage voltage at the first polarity for a reference dielectric layer having the same thickness as the test dielectric layer, wherein the reference dielectric layer comprises substantially none of a first material, and determining a value, $X_T$, indicative of a concentration of the first material in the test dielectric layer based on a relationship between $V_T$ and $V_R$.

Implementations of the method may include one or more of the following features and/or features of other aspects.

The method can include determining the thickness of the test dielectric layer. The method can also include determining the reference leakage voltage from the thickness of the test dielectric layer. Determining the thickness of the test dielectric layer can include measuring a leakage voltage, $V_{T2}$, at a second polarity opposite the first polarity, proportional to the test dielectric layer thickness. The thickness of the test dielectric layer, T, can be determined according to the equation $$T=(V_{T2}-B_{R2})/A_{R2},$$

wherein $B_{R2}$ and $A_{R2}$ are predetermined parameters relating a reference leakage voltage, $V_{R2}$, corresponding to a leakage voltage at the second polarity for a reference dielectric layer comprising substantially none of the first material to a thickness of the reference dielectric layer, $T_R$. In some embodiments, $V_{R2}=A_{R2}\times T_R+B_{R2}$.

The reference dielectric layer can include a reference dielectric material having a conduction band energy, $E_R^C$, and a valence band energy, $E_R^V$, and the first material can have a conduction band energy, $E_T^C$, and a valence band energy, $E_T^V$, and wherein measuring $V_T$ includes selecting the first polarity based on $E_R^C$, $E_R^V$, $E_T^C$, and $E_T^V$. The first polarity can be negative when $$|E_R^C-E_T^C|<|E_R^V-E^{TV}|.$$

The first polarity can be positive when $$E_R^C-E_T^C|>|E_R^V-E_T^V|.$$

Measuring $V_T$ can include depositing an ionic charge having the first polarity onto a surface of the test dielectric layer in an amount sufficient to cause a measurable leakage current to flow across the test dielectric layer, monitoring a voltage of the dielectric layer after depositing the ionic charge, and determining $V_T$ based on the monitored voltage.

$X_T$ can be proportional to a difference between $V_T$ and $V_R$. For example, $X_T$ can be determined according to the formula $$X_T=(V_T-V_R)/(V_{T2}-B_{R2}),$$

wherein $V_{T2}$ is a leakage voltage of the test dielectric layer at a second polarity opposite the first polarity and $B_{R2}$ is a predetermined parameter relating a reference leakage voltage, $V_{R2}$, corresponding to a leakage voltage at the second polarity for a reference dielectric layer comprising substantially none of the first material to a thickness of the reference dielectric layer, $T_R$.

The method can also include calculating the concentration, [X], of the first material in the test dielectric layer from $X_T$. [X] can be calculated according to the formula $$[X] = C_{CAL} \times X_T + D_{CAL},$$

wherein $C_{CAL}$ and $D_{CAL}$ are predetermined parameters relating [X] to $X_T$.

The first material can include nitrogen. The reference dielectric layer can include $SiO_2$.

In general, in a further aspect, the invention features a method for determining a composition of a test dielectric layer on a semiconductor substrate, which includes depositing an ionic charge of a first polarity onto a surface of the dielectric layer using a corona discharge, monitoring a voltage of the dielectric layer with a non-contact probe after depositing the ionic charge, determining a leakage voltage, $V_T$, for the test dielectric layer based on the monitored voltage, and calculating a value, $X_T$, indicative of a concentration of a first material in the test dielectric layer based on a difference between $V_T$ and a reference leakage voltage, $V_R$.

Implementations of the method can include one or more of the following features and/or features of other aspects.

$V_R$ can correspond to a leakage voltage at the first polarity for a reference dielectric layer having the same thickness as the test dielectric layer, wherein the reference dielectric layer comprises substantially none of the first material.

Calculating $X_T$ can include first determining $V_R$ from a thickness of the test dielectric layer. The thickness of the test dielectric layer can be determined by measuring a leakage voltage, $V_{T2}$, of the test dielectric layer for a second polarity opposite the first polarity, and calculating the thickness of the test dielectric layer using a function relating the thickness of a dielectric layer to its leakage voltage for the second polarity.

Embodiments of the invention can include one or more of the following advantages. Methods disclosed herein can be used to rapidly determine the composition of mixed dielectric layers (e.g., in a matter of minutes or less). Embodiments include non-contact methods for determining dielectric composition. These methods can utilize established corona charging and contact potential difference monitoring techniques and equipment. Extremely thin (e.g., less than about 5 nm, 3 nm, 2 nm, such as 1.3 nm or less) dielectric layers can be characterized, even in the presence of substantial leakage current using kinetic techniques for measuring leakage voltage. Static leakage voltage measurements can also be used.

The details of one or more embodiments of the invention are set forth in the accompanying drawings and the description below. Other features, objects, and advantages of the invention will be apparent from the description and drawings, and from the claims.

DESCRIPTION OF DRAWINGS

In FIG. 1A the scale on the leakage current axis is linear, while in FIG. 1B this scale is logarithmic.

Like reference symbols in the various drawings indicate like elements.

DETAILED DESCRIPTION

When ionic charge is deposited on a surface of a dielectric layer, the voltage across the dielectric layer, $V_D$, depends not only on the amount of deposited charge, but also on the composition of the dielectric layer. Accordingly, the behavior of dielectric voltage as a function of charge deposited on its surface, known as the charge-voltage characteristic, can be used to determine the dielectric layer's composition, provided certain other information about the dielectric layer is known (e.g., the layer's thickness). One way to compare the charge-voltage characteristics of various dielectric layers is to compare a dielectric voltage indicative of a certain phenomenon that occurs in the dielectric layer. For example, one can compare the leakage voltage of different dielectric layers. The leakage voltage for a test dielectric layer, $V_T$, is a voltage at which leakage current (i.e., electric current through the dielectric layer) is high (e.g., more than about $10^{-7}$ A/cm$^2$). A variety of methods can be used for measuring leakage voltage, some of which are described below.

In some mixed dielectrics, the dielectric layer includes of a primary dielectric material mixed with another material. For example, an oxynitride (Si—O—N) dielectric includes silicon oxide ($SiO_2$) and silicon nitride ($Si_3N_4$). To determine the nitrogen concentration in an oxynitride, the leakage voltage for an oxynitride layer under test is compared to a leakage voltage for a $SiO_2$ dielectric layer the same thickness as the oxynitride layer. In other words, $V_T$ is compared to $V_R$, the leakage voltage for a reference layer (e.g., the $SiO_2$ layer). The difference between $V_T$ and $V_R$ is related to the nitride concentration in the test layer. Thus, when appropriately normalized and calibrated, the difference between the leakage voltage of the reference layer and the test layer provides a measure of the mixed dielectric layer's composition.

Figure 1A:
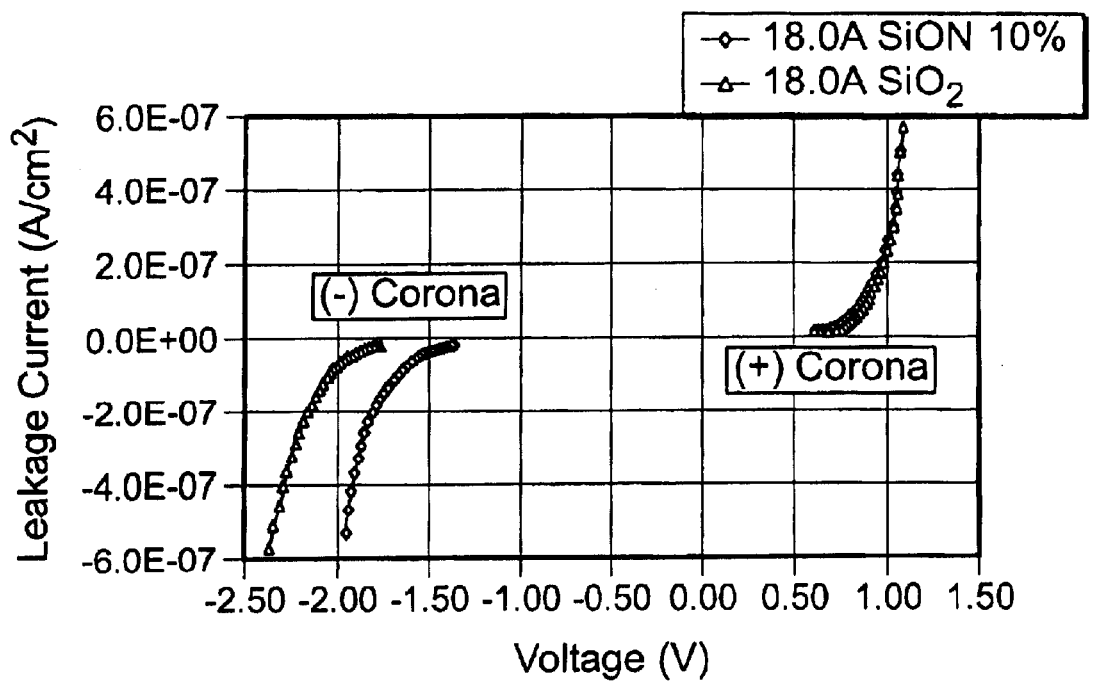
FIG. 1A and FIG. 1B are plots showing leakage current as a function of voltage for an 18 Angstrom thick $SiO_2$ layer and an 18 Angstrom thick oxynitride layer with 10% nitrogen.
Figure 1B:
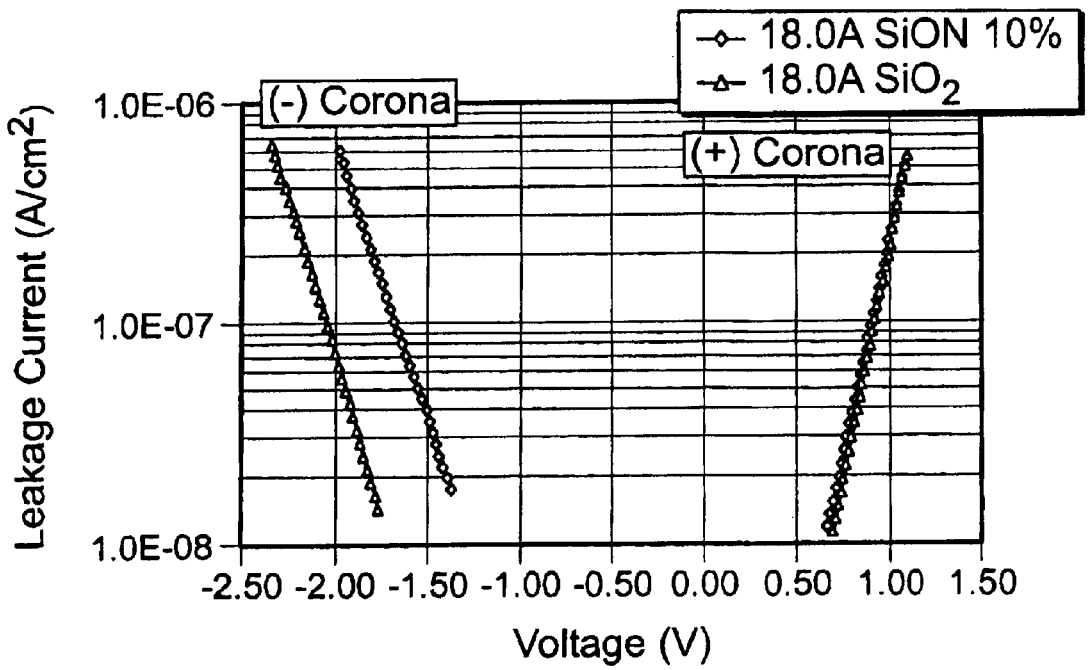

Generally, leakage voltage can be measured for either polarity of the deposited charge (i.e., positive or negative). However, in many cases, the difference in leakage voltage between the reference and test layer is greater for one polarity. For example, referring to FIGS. 1A and 1B, which show leakage current as a function of voltage for a Si—O—N test layer and a $SiO_2$ reference layer, the characteristics of the reference layer differ from the test layer substantially more for negative deposited charge (i.e., negative voltage) than for positive deposited charge. In this example, there is an approximately 0.4 V shift in leakage voltage for negative charge, where leakage voltage is taken as the onset voltage of measurable leakage current. On the other hand, for positive charge the data for the test and reference layers are very similar and practically merge for leakage currents greater than about $10^{-7}$ A/cm$^2$. Accordingly, the composition of the test layer should be determined using negative polarity in this case.

Figure 2:
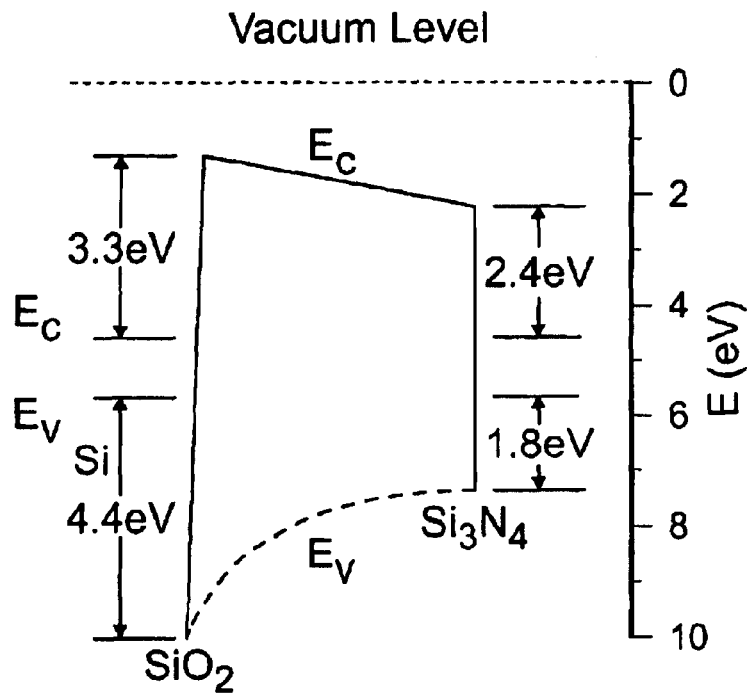
FIG. 2 is a plot showing the valence and conduction band energies for $SiO_2$ and $Si_3N_4$ relative to Si.

The sensitivity of a test layer to deposited charge polarity can be understood by considering the energy band structure of the primary and secondary dielectric material in the test layer and the underlying semiconductor. Leakage current is due charge carriers injected into the dielectric layer from the semiconductor substrate tunneling across the dielectric layer. This tunneling current depends on an energy barrier between the substrate and the dielectric layer. When the deposited charge is negative, tunneling depends on the offset between the valence bands of the dielectric and semiconductor, while for positive deposited charge tunneling depends on the conduction band offset. Referring to FIG. 2, the addition of nitrogen to $SiO_2$, for example, causes a large decrease in the valence band offset, but not the conduction band offset. In particular, the valance band offset for silicon nitride is 1.8 eV relative to silicon, 2.4 times less than the 4.4 eV band offset for $SiO_2$. Thus, the addition of nitrogen to $SiO_2$ shifts the valence band offset to a lower value and lowers the voltage at which leakage current appears. On the other hand, the difference between the conduction band offset between $Si_3N_4$ and Si and between $SiO_2$ and Si is significantly less (i.e., 2.4 eV–3.3 eV=–0.9 eV), causing substantially less variation between the leakage voltages at positive polarity.

Figure 3:
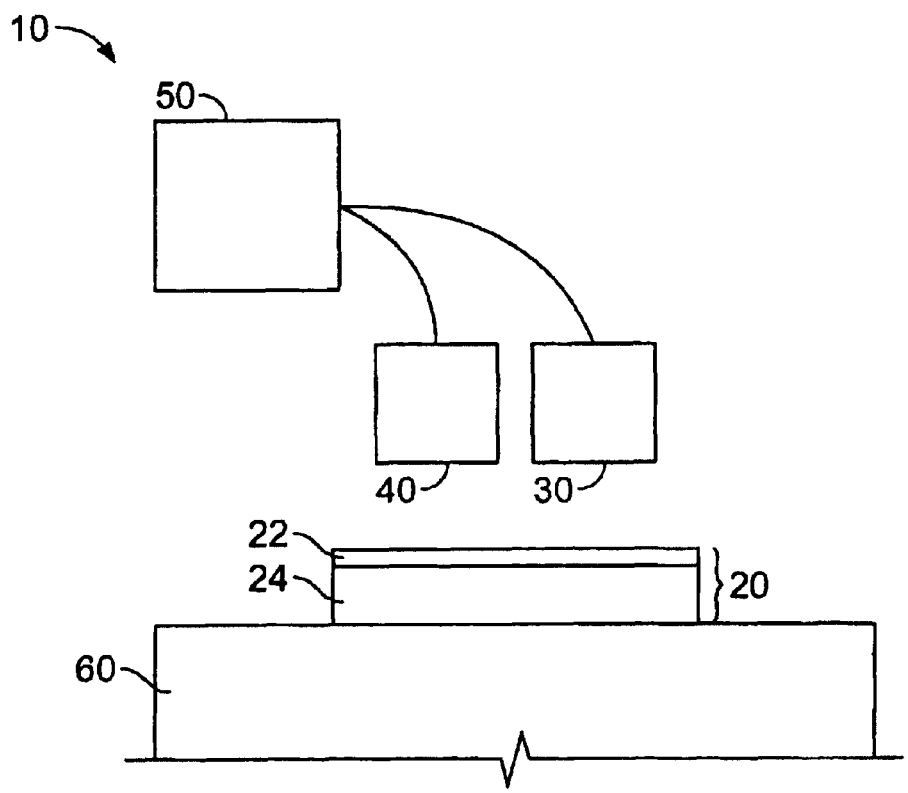
FIG. 3 is a schematic diagram of a wafer testing system.

The leakage voltage of a test layer can be measured using corona discharge and a non-contact probe. For example, referring to FIG. 3, a wafer test system 10 is configured to measure a leakage voltage of a dielectric layer 22 disposed on a semiconductor substrate 24 of a test wafer 20. Wafer test system 10 includes a corona source 30 and a non-contact voltage probe 40, both under the control of a computer 50. An example of test system 10 is described in U.S. Pat. No. 6,538,462 by Lagowski et al., which is incorporated herein in its entirety by reference.

During operation, corona source 30 deposits ionic charge doses on the exposed surface of dielectric layer 22. After each dose, voltage probe 40 monitors a contact potential difference between the probe and a grounded chuck 60 in electrical contact with the surface of substrate 24. Corona discharge in air can be achieved by applying a DC voltage (e.g., about 5 to 10 kV) to a needle or thin wire electrode placed about 1 cm above the surface of dielectric layer 22. The corona discharge creates ions of the same polarity (i.e., positive or negative) as that of the DC voltage. Ions created in discharge diffuse toward and attach to the dielectric surface due to an electrostatic interaction.

Voltage measurements using voltage probe 40 are performed after charging by moving wafer 20 relative to test system 10 so that the charged region is positioned proximate to probe 40. The non-contact voltage measurement, also referred to as the contact potential difference, is performed by a probe with a vibrating reference electrode or a probe with a vibrating fork between the electrode and the dielectric surface. The vibrating electrode configuration is referred to as a Kelvin probe (commercially available from Trek, Inc., Medina, N.Y.), and the vibrating fork configuration is referred to as a Monroe probe (commercially available from Monroe Electronics, Lyndonville, N.Y.). The electrode forms a capacitor with semiconductor substrate 24. The vibrations cause a periodic change in the capacitance of this capacitor, which is reflected by the probe voltage measurement.

Each case, system 10 measures a contact potential difference, $V_{CPD}$, which can be expressed as $$V_{CPD} = V_D + V_{SB} + \Phi_{ms}, \tag{1}$$

where $V_D$ is the voltage drop across dielectric layer 22, $V_{SB}$ is a surface barrier voltage of semiconductor substrate 24, and $\Phi_{ms}$ is a work function difference between voltage probe 40 and semiconductor substrate 24. For a corona charge dose $\Delta Q_c$, deposited on the surface of dielectric layer 22, $V_D$ changes by an amount $\Delta V_D$, given by $$\Delta V_D = \frac{\Delta Q_c}{C_D}, \tag{2}$$

where $C_D$ is the capacitance of dielectric layer 22. The corona charge also induces a change in the semiconductor surface barrier, $\Delta V_{SB}$, but does not affect $\Phi_{ms}$.

Test system 10 can be used in number of ways to measure a leakage voltage of dielectric layer 22. The different techniques can be broadly categorized as being either static or kinetic. Static measurements are best suited to dielectric films that show low leakage, and thus minimal corona charge neutralization during a charging-measuring cycle. In other words, a voltage change $\Delta V_{CPD}$ caused by the application of a corona charge dose $\Delta Q_c$ does not vary substantially with time (i.e., for the duration of a measurement cycle). In static measurements, using a sequence of charging-measuring steps, test system 10 acquires a set of charge-voltage data, referred to as the charge-voltage characteristic for the dielectric layer. In some embodiments, the leakage voltage is the tunneling voltage, which corresponds to a saturation voltage in the charge-voltage characteristic. Saturation refers to the dielectric voltage at which addition deposited corona charge is neutralized due to leakage current. Thus, for increasing corona charge, the dielectric voltage remains substantially unchanged once saturation is reached. The voltage at which saturation occurs is also referred to as the tunneling voltage, $V_{TUNNEL}$, as it corresponds to the voltage at which charge begins to tunnel through the dielectric layer.

The tunneling voltage, as measured using the above-described method, can depend on the corona charging parameters, such as the corona ion flux, $I_c$, used to obtain each charge dose, $\Delta Q_c$, and the time interval between charging and monitoring the voltage. Due to this dependence, $V_{TUNNEL}$ measured using a high ion flux (e.g., about $10^6$ C/cm²s) and a short time interval between charging and monitoring (e.g., about one second) may be appreciably larger that that for low flux (e.g., about $10^{-8}$ C/cm²s) and a long time interval (e.g., about 100 seconds) even though the charge dose, $\Delta Q_c$, in both cases is the same.

Examples of static measurement methods are described by D. K. Schroder in the review article entitled "Surface voltage and surface photovoltage: history, theory and applications," *Meas. Sci. Technol.* 12 (2001) R16–R31, the entire contents of which are hereby incorporated by reference. Static measurement methods for determining a leakage voltage (i.e., saturation voltage) are disclosed in U.S. Pat. No. 6,097,196 and U.S. Pat. No. 6,011,404, the entire contents both of which are hereby incorporated by reference.

Where the effects of leakage in the dielectric layer are significant (e.g., for very thin dielectrics, such as dielectrics less than about 10 nm thick), kinetic measurements are better suited for determining the leakage voltage. Kinetic measurements involve monitoring the dielectric voltage as a function of time after each corona dose. Due to the time-resolved voltage measurements, the charge-voltage characteristic can be corrected for the effects of leakage. Furthermore, a kinetic measurement provides a means for monitoring the current-voltage characteristic of a dielectric film. The dielectric leakage current, $I_D$, can be determined from the time derivative of the measured voltage, using the relationship $$I_D = C_D \times \frac{dV}{dt},\qquad(3)$$

where $C_D$ is the capacitance of the dielectric layer.

In some embodiments that use kinetic measurements, the leakage voltage can be determined from the dielectric voltage monitored following cessation of a charging. For example, the dielectric voltage can be measured once a self-adjusting steady state condition is created on the surface of the dielectric layer by an intense but brief corona charging pulse. In the self-adjusting steady state condition, the corona flux, $I_c$, is balanced by the dielectric leakage current, $I_D$. In such embodiments, the leakage voltage can be the initial voltage, $V_t=0$, determined by extrapolating the measured voltage as a function of time back to the moment when charging ceases. Alternatively, the leakage voltage can be determined as the dielectric voltage measured a predetermined delay time after charging ceases (e.g., such as between about 0.5 and 2 seconds, such as 1.2 seconds). Such delayed voltage measurements can be substantially insensitive to corona flux and to the duration of the charging pulse.

Examples of kinetic methods are described in U.S. Pat. No. 6,538,462, and in U.S. patent application Ser. No. 09/810,789, entitled "STEADY STATE METHOD FOR MEASURING THE THICKNESS AND THE CAPACITANCE OF ULTRA THIN DIELECTRIC IN THE PRESENCE OF SUBSTANTIAL LEAKAGE CURRENT," filed on Mar. 16, 2001, the entire contents both of which are hereby incorporated by reference.

Figure 4A:
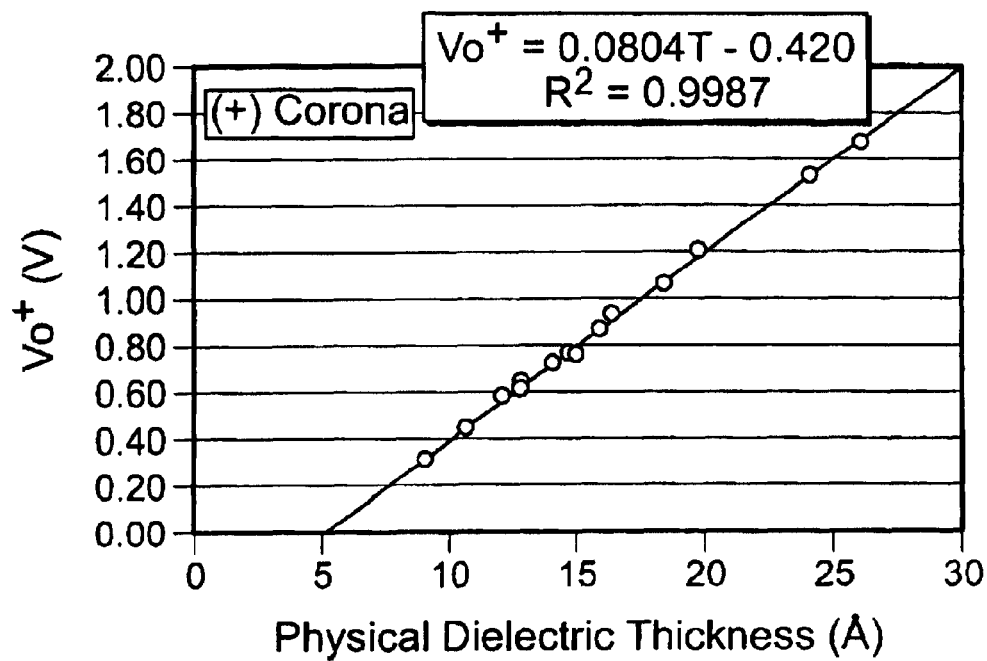
FIG. 4A and FIG. 4B are plots showing the leakage voltage for an $SiO_2$ layer as a function of thickness for positive and negative polarity, respectively.
Figure 4B:
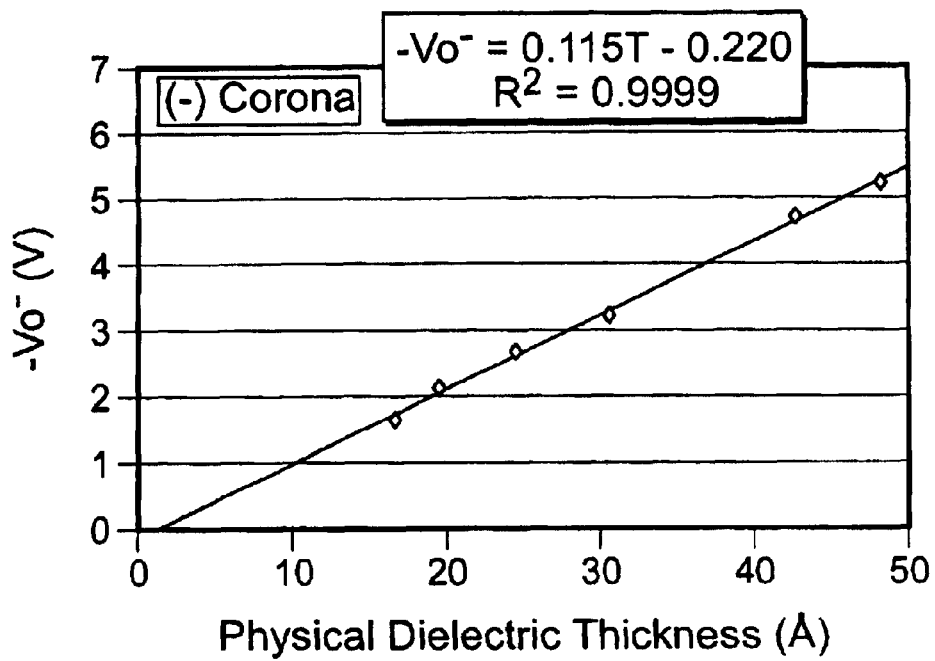

The leakage voltage for a test layer typically depends on the layer's thickness, T, in addition to the secondary dielectric concentration, thus the layer's thickness should be determined (if not already known) in order to determine composition. In some dielectrics, the leakage voltage is proportional to the layer thickness. Referring to FIGS. 4A and 4B, for example, dielectric thickness for $SiO_2$ for both positive (FIG. 4A) and negative (FIG. 4B) polarity is substantially proportional to leakage voltage. Thus, for each polarity, the relationship between thickness and leakage voltage can be characterized by a proportionality constant, $A_R^{+(-)}$, and an offset constant $B_R^{+(-)}$, where $$V_R^{+(-)} = A_R^{+(-)} \times T + B_R^{+(-)}\qquad(4)$$

where the superscript +(−) refers to positive (negative) polarity, and the subscript R refers to the reference dielectric (in this example $SiO_2$). As is apparent from FIG. 4A and FIG. 4B, the proportionality constant and offset voltages are not necessarily the same for different polarity. In the example shown, $A_R^+=0.0804$ V/Å and $B_R^+=0.420$ V while $A_R^-=-0.115$ V/Å and $B_R^-=0.220$ V.

Dielectric layer thickness can be determined by a variety of means. One method for determining film thickness is disclosed in aforementioned U.S. patent application Ser. No. 09/810,789 using kinetic dielectric voltage measurements. Alternatively, dielectric film thickness can be determined using static dielectric voltage measurements, as described in the aforementioned reference by Schroder, for example.

For a mixed dielectric layer where the charge-voltage characteristic does not differ dramatically from the reference dielectric material for one polarity, a measurement of the leakage voltage at that polarity can be used to determine the thickness of the test dielectric. In particular, $V_T$ is assumed equal to $V_R$, for this polarity. Thus, T can be readily determined from $A_R^*$ and $B_R^*$ as $$T = \frac{V_T^* - B_R^*}{A_R^*}\qquad(5)$$

where the superscript "*" refers to the polarity at which the test layer's charge-voltage characteristics are similar to a reference layer. In other words, the thickness of the test layer is taken to be equal to the thickness of a reference layer that would have the same leakage voltage at that polarity.

Once film thickness is known, the leakage voltage of the test layer, $V_T$, is compared to the leakage voltage of a reference layer of the same thickness, $V_R$. The difference between these leakage voltages provides an offset voltage, given as $$\Delta V = |V_T - V_R|.\qquad(6)$$

The offset voltage is related to the concentration of secondary dielectric material in the test layer and using appropriate calibration data can be converted to a value, $X_T$, proportional to the dopant concentration. $X_T$ is also referred to as an "indicator." For example, where the secondary dielectric is $Si_3N_4$, $X_T$ is referred to as the nitrogen indicator.

The calibration data relating the offset voltage to the indicator can be determined empirically or from theory. In some embodiments, the indicator can de determined from the equation $$X_T = \frac{\Delta V^{+(-)}}{V_R^{-(+)} - B_R^{-(+)}},\qquad(7)$$

where $B_R^{+(-)}$ refers to the offset constant for the reference dielectric at +(−) polarity.

Once the indicator is found, the concentration, [X], of the secondary dielectric material can be determined using premeasured calibration constants $C_{CAL}$ and $D_{CAL}$, where $$[X] = C_{CAL} X_T + D_{CAL}.\qquad(8)$$

Typically, calibration constants $C_{CAL}$ and $D_{CAL}$ are determined empirically by independently measuring [X] using some other means and comparing it to the indicator. [X] can be independently measured using X-ray Photoelection Spectroscopy or Secondary Ion Emission Spectroscopy, for example. A linear regression can be used to determine $C_{CAL}$ and $D_{CAL}$ from the $X_T$/[X] data.

Figure 5:
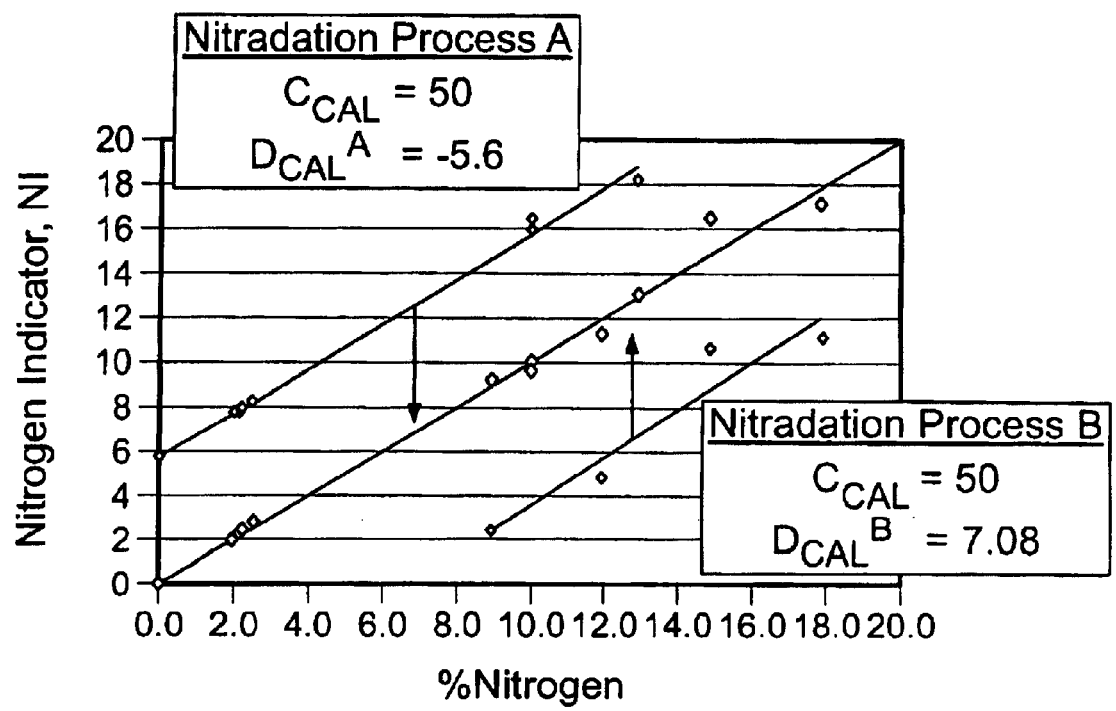
FIG. 5 is a plot showing the relationship between nitrogen concentration and the nitrogen indicator for two different processing tools that introduce nitrogen to $SiO_2$.

Calibration constants $C_{CAL}$ and $D_{CAL}$ can vary depending on how the test layer was prepared, thus appropriate constants should be selected according to the dielectric layer preparation method. For example, referring to FIG. 5, $D_{CAL}$ for converting the nitrogen indicator to nitrogen concentration differs for two test wafers prepared by treatment of $SiO_2$ with plasma containing nitrogen using two different plasma tools manufactured by different suppliers; A and B respectively. As shown in FIG. 5, in both cases $C_{CAL}=50$, however for process "A" (i.e. tool from manufacturer A) $D_{CAL}=5.6$ while $D_{CAL}=-7.8$ for process "B" (i.e. tool from manufacturer B).

Figure 6:
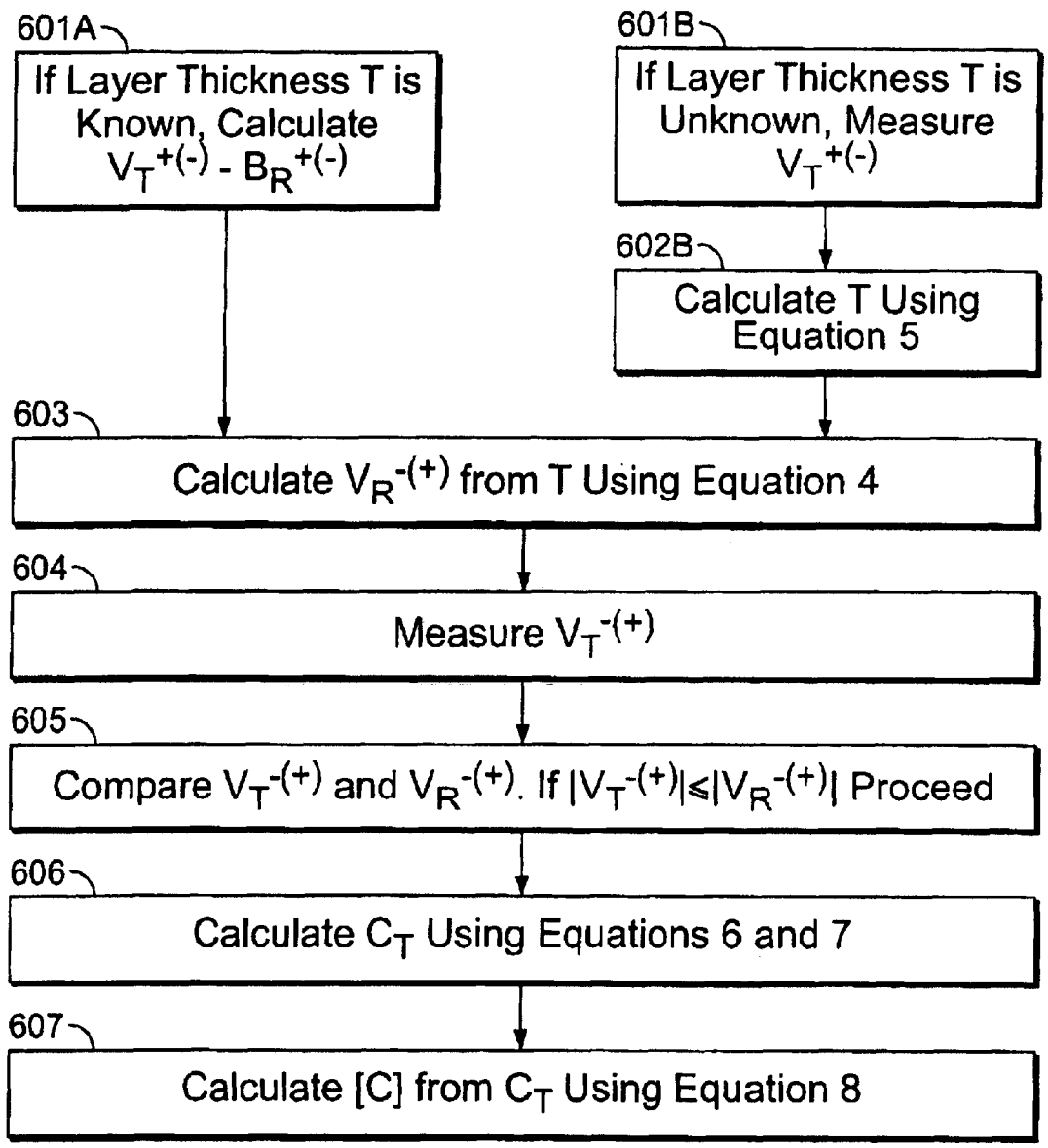
FIG. 6 is a flow chart showing methods for determining the concentration of nitrogen in a dielectric layer.

The above-described method for determining mixed dielectric composition is summarized in a flow-chart, shown in FIG. 6. If the dielectric layer thickness is known, calculate $V_T^{+(-)}$ from Equation 4, assuming that $V_T^{+(-)} \approx V_R^{+(-)}$. Here, superscript +(−) refers to the polarity at which the test and reference dielectric charge-voltage characteristics are approximately equal. Once $V_T^{+(-)}$ is known, calculate $V_T^+{}_{(-)}-B_R^{+(-)}$ (step 601A). If dielectric thickness is unknown, measure $V_T^{+(-)}$ (step 601B), and calculate the dielectric thickness using Equation 5 (step 602B). Next, calculate $V_R^{-(+)}$ from the layer thickness using Equation 4 (step 603). Measure the dielectric leakage voltage, $V_T^{-(+)}$, (step 604) and compare $V_T^{-(+)}$ to $V_R^{-(+)}$. In embodiments where the addition of the secondary dielectric reduces the tunneling barrier energy, $|V_T^{-(+)}|$ should be less than or equal to $|V_R^{-(+)}|$ (step 605). In such embodiments, if $|V_T^{-(+)}| \leq |V_R^{-(+)}|$ the indicator should produce a meaningful result. Calculate the indicator, $X_T$, according to Equations 6 and 7 (step 606), and calculate the concentration of the secondary dielectric from $X_T$ using Equation 8 (step 607).

This process is described for specific examples below. Although these examples describe determining nitrogen concentration in an oxynitride dielectric layer, the techniques disclosed herein can be applied to other types of mixed dielectric as well. For example, the techniques may be adapted to measure the concentration of hafnium in an Si—Hf—O dielectric layer, the concentration of zirconium in an Si—Zr—O dielectric layer. Examples of other mixed dielectric materials include Al—Hf—O and Al—Zr—O.

Furthermore, although Equation 8 infers a linear relationship between [X] and $X_T$, in other embodiments the relationship between these parameters can have other functional forms (e.g., can be polynomial). Generally, the relationship (e.g., polynomial coefficients) between [X] and $X_T$ can be determined empirically using $X_T$ vs. concentration data.

EXAMPLES

In the following examples, leakage voltage was determined using self-adjusting steady-state measurements of delayed voltage (i.e., measured 1.2 seconds after cessation of charging) using a FAaST™ tool with SASS™ option manufactured by Semiconductor Diagnostics, Inc. (Tampa, Fla.). Corona charging flux of $2 \times 10^{-6}$ C/cm²s was used for 3 seconds.

Example 1

Figure 7:
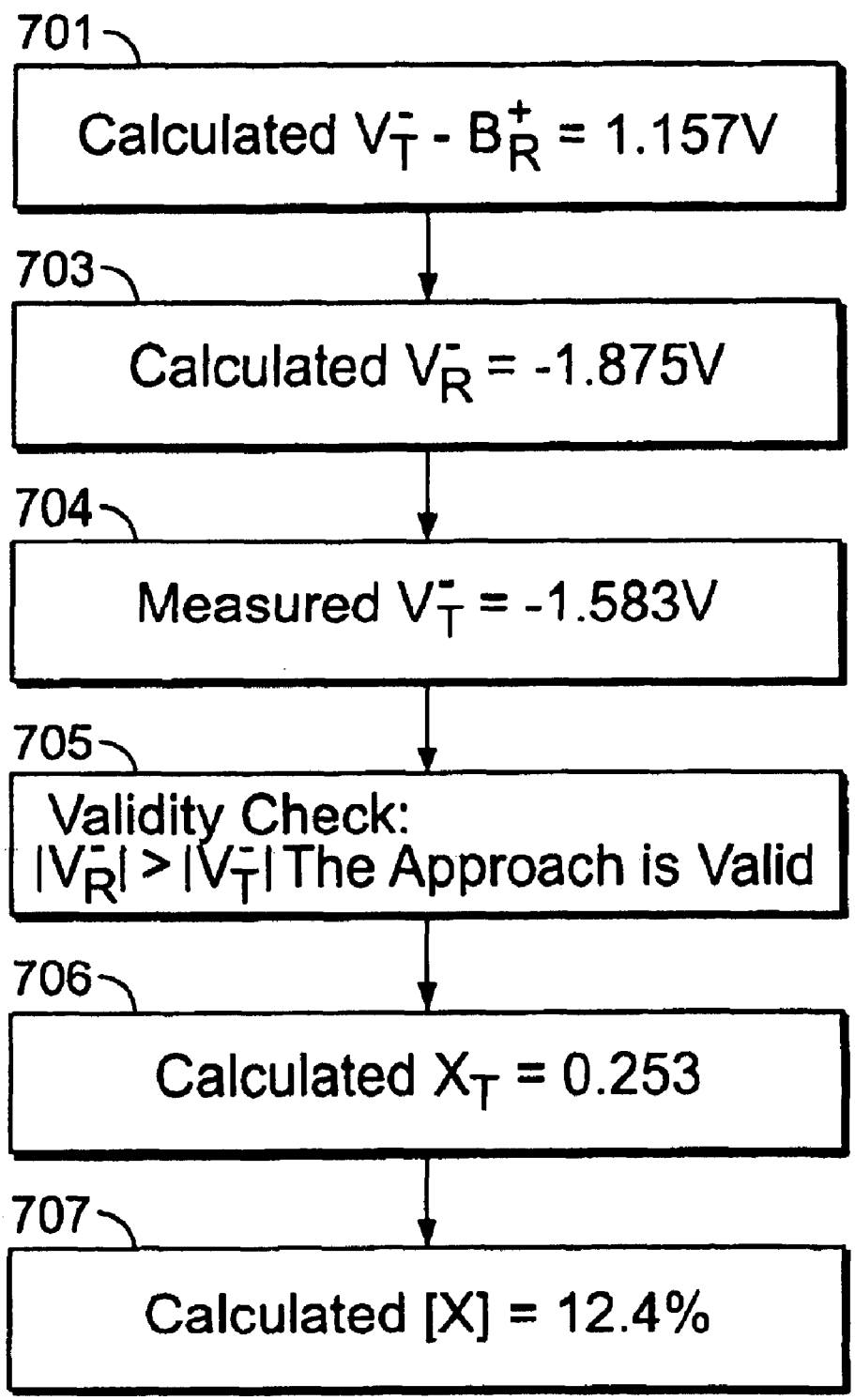
FIG. 7 is a flow chart showing the calculation of nitrogen concentration in an $SiO_2$ layer of known thickness.

Determination of Nitrogen Concentration in an Oxynitride Film of Known Thickness Referring to FIG. 7, $V_T^- - B_R^+$ was determined to be 1.157 V from film thickness, 14.44 Angstroms and reference data (step 701). The thickness was also used to determine $V_R^-$, −1.875 V, using Equation 4 (step 703). Using the above-mentioned wafer test system, the leakage voltage for negative charge was measured to be −1.583 V (step 704). The methodology was validated by checking that the magnitude of $V_R^-$ was greater than the magnitude of $V_T^-$ (step 705). The nitrogen indicator was calculated using Equations 6 and 7, yielding a value $X_T$=0.253 (step 706). Finally, the nitrogen concentration was determined to be 12.4% using Equation 8 (step 707).

Example 2

Figure 8:
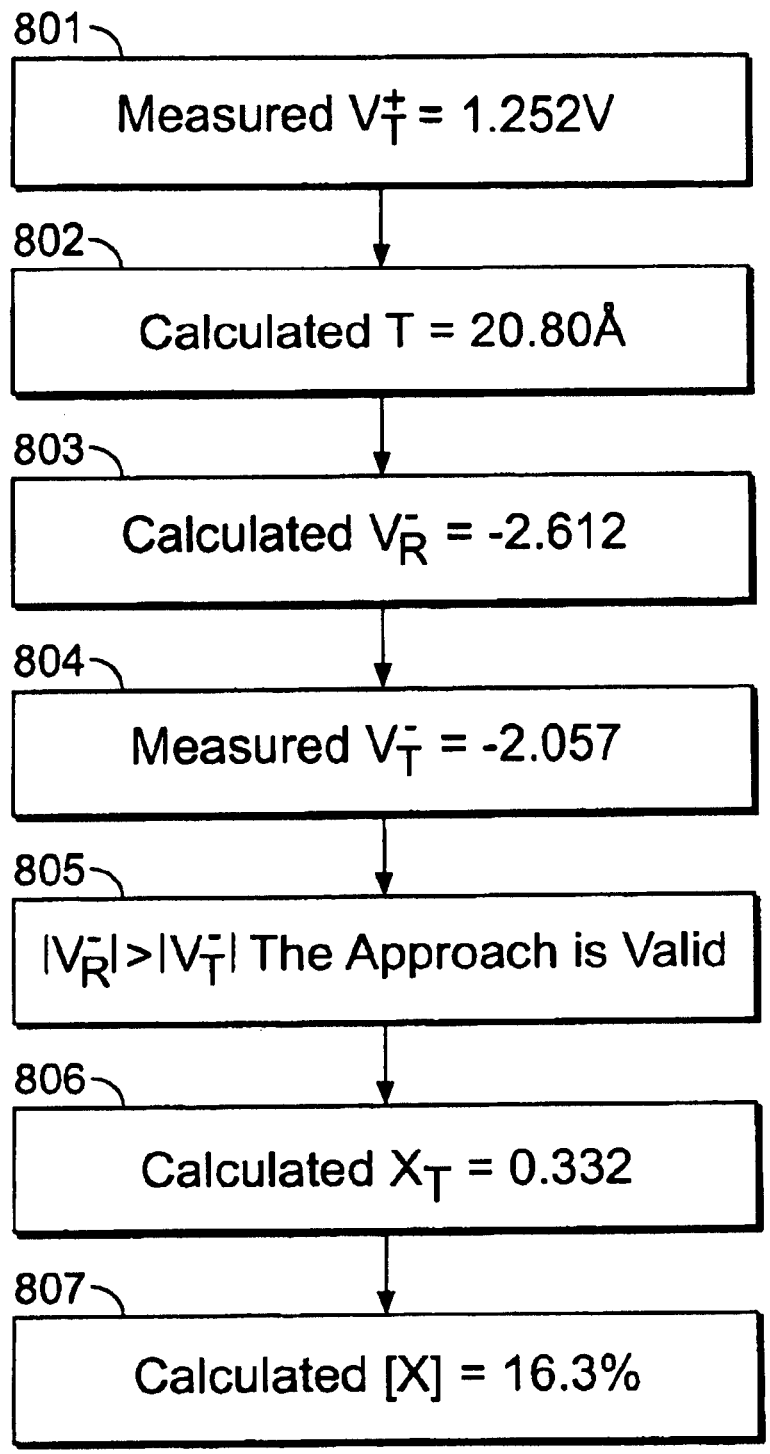
FIG. 8 is a flow chart showing the calculation of nitrogen concentration in an $SiO_2$ layer of unknown thickness.

Determination of Nitrogen Concentration in an Oxynitride Film of Unknown Thickness Referring to FIG. 8, $V_T^+$ was measured to be 1.252 V (step 801), from which the oxynitride's thickness was determined to be 20.80 Angstroms (step 802). Using Equation 4 and the film thickness, $V_R^-$ was calculated to be −2.612 V (step 803). $V_T^-$ was measured to be −2.057 V (step 804). Because the magnitude of $V_R^-$ was greater than the magnitude of $V_T^-$, the methodology was confirmed to be valid (step 805). Subsequently, the nitrogen indicator was calculated as 0.332 (step 806), from which the nitrogen concentration was calculated at 16.3% (step 807).

A number of embodiments of the invention have been described. Nevertheless, it will be understood that various modifications may be made without departing from the spirit and scope of the invention. Accordingly, other embodiments are within the scope of the following claims.

What is claimed is:

1. A method for determining a composition of a dielectric layer on a semiconductor substrate, the method comprising:

monitoring a voltage across the dielectric layer under conditions where substantial leakage current flows across the dielectric layer;

determining a leakage voltage for the dielectric layer from the monitored voltage; and determining the composition of the dielectric layer by comparing the leakage voltage to a reference voltage corresponding to the leakage voltage of a dielectric layer of known composition.

2. The method of claim 1, wherein the conditions where substantial leakage current flows across the dielectric layer are achieved by depositing an electric charge on a surface of the dielectric layer using a corona discharge.

3. The method of claim 2, wherein the voltage across the dielectric layer is monitored using a vibrating probe placed in proximity to the surface of the dielectric layer.

4. The method of claim 1, wherein the dielectric layer comprises first and second component materials, and the voltage across the dielectric layer is monitored for a polarity at which current-voltage characteristics for the first and second component materials differ the most.

5. A method for determining a composition of a test dielectric layer on a semiconductor substrate, the method comprising:

measuring a leakage voltage, $V_T$, at a first polarity for the test dielectric layer;

comparing $V_T$ to a reference leakage voltage, $V_R$, corresponding to a leakage voltage at the first polarity for a reference dielectric layer having the same thickness as the test dielectric layer, wherein the reference dielectric layer comprises substantially none of a first material; and determining a value, $X_T$, indicative of a concentration of the first material in the test dielectric layer based on a relationship between $V_T$ and $V_R$.

6. The method of claim 5, further comprising determining the thickness of the test dielectric layer.

7. The method of claim 6, further comprising determining the reference leakage voltage from the thickness of the test dielectric layer.

8. The method of claim 7, wherein determining the thickness of the test dielectric layer comprises measuring a leakage voltage, $V_{T2}$, at a second polarity opposite the first polarity, proportional to the test dielectric layer thickness.

9. The method of claim 8, wherein the thickness of the test dielectric layer, T, is determined according to the equation $$T = (V_{T2} - B_{R2})/A_{R2},$$

wherein $B_{R2}$ and $A_{R2}$ are predetermined parameters relating a reference leakage voltage, $V_{R2}$, corresponding to a leakage voltage at the second polarity for a reference dielectric layer comprising substantially none of the first material to a thickness of the reference dielectric layer, $T_R$.

10. The method of claim 9, wherein $V_{R2}=A_{R2} \times T_R + B_{R2}$.

11. The method of claim 5, wherein the reference dielectric layer comprises reference dielectric material having a conduction band energy, $E_R^C$, and a valence band energy, $E_R^V$, and the first material has a conduction band energy, $E_T^C$, and a valence band energy, $E_T^V$, and wherein measuring $V_T$ comprises selecting the first polarity based on $E_R^C$, $E_R^V$, $E_T^C$, and $E_T^V$.

12. The method of claim 11, wherein the first polarity is negative when $$|E_R^C - E_T^C| < |E_R^V - E^{TV}|.$$

13. The method of claim 11, wherein the first polarity is positive when $$|E_R^C - E_T^C| > |E_R^V - E_T^V|.$$

14. The method of claim 5, wherein measuring $V_T$ comprises:
 depositing an ionic charge having the first polarity onto a surface of the test dielectric layer in an amount sufficient to cause a measurable leakage current to flow across the test dielectric layer;
 monitoring a voltage of the dielectric layer after depositing the ionic charge; and
 determining $V_T$ based on the monitored voltage.

15. The method of claim 5, wherein $X_T$ is proportional to a difference between $V_T$ and $V_R$.

16. The method of claim 15, wherein $X_T$ is determined according to the formula $$X_T = (V_T - V_R)/(V_{T2} - B_{R2}),$$

wherein $V_{T2}$ is a leakage voltage of the test dielectric layer at a second polarity opposite the first polarity and $B_{R2}$ is a predetermined parameter relating a reference leakage voltage, $V_{R2}$, corresponding to a leakage voltage at the second polarity for a reference dielectric layer comprising substantially none of the first material to a thickness of the reference dielectric layer, $T_R$.

17. The method of claim 5, further comprising calculating the concentration, [X], of the first material in the test dielectric layer from $X_T$.

18. The method of claim 17, wherein [X] is calculated according to the formula $$[X] = C_{CAL} \times X_T + D_{CAL},$$

wherein $C_{CAL}$ and $D_{CAL}$ are predetermined parameters relating [X] to $X_T$.

19. The method of claim 5, wherein the first material comprises nitrogen.

20. The method of claim 19, wherein the reference dielectric layer comprises $SiO_2$.

21. A method for determining a composition of a test dielectric layer on a semiconductor substrate, the method comprising:
 depositing an ionic charge of a first polarity onto a surface of the dielectric layer using a corona discharge;
 monitoring a voltage of the dielectric layer with a non-contact probe after depositing the ionic charge;
 determining a leakage voltage, $V_T$, for the test dielectric layer based on the monitored voltage; and
 calculating a value, $X_T$, indicative of a concentration of a first material in the test dielectric layer based on a difference between $V_T$ and a reference leakage voltage, $V_R$.

22. The method of claim 21, wherein $V_R$ corresponds to a leakage voltage at the first polarity for a reference dielectric layer having the same thickness as the test dielectric layer, wherein the reference dielectric layer comprises substantially none of the first material.

23. The method of claim 21, wherein calculating $X_T$ comprises first determining $V_R$ from a thickness of the test dielectric layer.

24. The method of claim 23, wherein the thickness of the test dielectric layer is determined by measuring a leakage voltage, $V_{T2}$, of the test dielectric layer for a second polarity opposite the first polarity, and calculating the thickness of the test dielectric layer using a function relating the thickness of a dielectric layer to its leakage voltage for the second polarity.

* * * * *